(12) United States Patent
Housman et al.

(10) Patent No.: US 12,349,894 B2
(45) Date of Patent: Jul. 8, 2025

(54) SUTURE ANCHOR INSERTION ASSEMBLIES AND METHODS OF USE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Mark E. Housman, North Attleboro, MA (US); Jon-Paul Rogers, North Smithfield, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 292 days.

(21) Appl. No.: 17/920,531

(22) PCT Filed: Apr. 29, 2021

(86) PCT No.: PCT/US2021/029842
§ 371 (c)(1),
(2) Date: Oct. 21, 2022

(87) PCT Pub. No.: WO2021/225858
PCT Pub. Date: Nov. 11, 2021

(65) Prior Publication Data
US 2023/0149009 A1    May 18, 2023

Related U.S. Application Data

(60) Provisional application No. 63/020,762, filed on May 6, 2020.

(51) Int. Cl.
*A61B 17/04* (2006.01)

(52) U.S. Cl.
CPC ...... *A61B 17/0401* (2013.01); *A61B 17/0483* (2013.01); *A61B 2017/0409* (2013.01); *A61B 2017/044* (2013.01); *A61B 2017/0445* (2013.01)

(58) Field of Classification Search
CPC ............ A61B 17/0401; A61B 17/0483; A61B 2017/0409; A61B 2017/044; A61B 2017/0445; A61B 2017/0458; A61B 2017/06057
See application file for complete search history.

(56) References Cited

U.S. PATENT DOCUMENTS

| 8,882,801 | B2 * | 11/2014 | DiMatteo | A61B 17/0401 606/232 |
| 2010/0069923 | A1 * | 3/2010 | Nguyen | A61B 17/0401 606/232 |
| 2013/0178901 | A1 * | 7/2013 | Arai | A61F 2/0805 606/233 |
| 2019/0350577 | A1 * | 11/2019 | Norton | A61F 2/0811 |
| 2021/0369261 | A1 * | 12/2021 | Patrinicola | A61B 17/1615 |

* cited by examiner

*Primary Examiner* — Sarah A Long
(74) *Attorney, Agent, or Firm* — ArentFox Schiff LLP; Joseph M. Maraia; Marlo Schepper Grolnic

(57) ABSTRACT

Suture anchor insertion assemblies include needles pre-attached to suture or suture tape, which reside within a housing of an inserter. The suture extends around a suture bridge of a suture anchor having at least one rib extending through the internal volume. An outer surface of the shaft of the inserter includes a groove sized to receive both the rib of the suture anchor and the length of suture while still allowing the suture to slide relative to the inserter.

20 Claims, 12 Drawing Sheets

SUTURE ANCHOR INSERTION ASSEMBLIES AND METHODS OF USE

CROSS-REFERENCE TO RELATED APPLICATIONS

This application is the U.S. national phase entry under 35 U.S.C. § 371 of International Application No. PCT/US2021/029842, filed Apr. 29, 2021, entitled SUTURE ANCHOR INSERTION ASSEMBLIES AND METHODS OF USE, which in turn claims priority to and benefit of U.S. Provisional Application No. 63/020,762, filed May 6, 2020, the contents of which are incorporated herein by reference in their entirety for all purposes.

FIELD

The present disclosure relates to surgical repair of tissue and, more specifically, to devices and methods for inserting a suture anchor used in such repair.

BACKGROUND

During surgical repair of tissue, surgeons commonly use suture anchors to attach the tissue or a tissue graft to bone. Typically, a surgeon uses an inserter tool to implant a suture anchor into a drilled bore in bone. In some case, the surgeon also connects one or more sutures or suture tape with attached needles to the suture anchor. The surgeon uses the needles to pass the suture through tissue and subsequently ties the suture to secure the tissue to the bone.

Some suture anchor inserters store both a portion of the suture and pre-attached needles within the handle, allowing for easy deployment by the user. In addition, such inserters provide tension on the suture, allowing the suture anchor to remain engaged with the inserter during the repair. However, problems occur by having needles pre-attached to the sutures and stored within the inserter. The needles cannot pass through the center of the inserter shaft without requiring an open slot in the shaft, which can weaken the insertion properties of the inserter. Also, misalignment of the inserter to the suture anchor, as well as an improper size or volume of suture and/or suture tape, can prevent suture slide after inserting the suture anchor into bone.

SUMMARY

Suture anchor insertion assemblies described herein include needles pre-attached to suture or suture tape, which reside within a housing of an inserter. The suture extends around a suture bridge of a suture anchor having at least one rib extending through the internal volume. An outer surface of the shaft of the inserter includes a groove sized to receive both the rib of the suture anchor and the length of suture while still allowing the suture to slide relative to the inserter. The suture anchor insertion assemblies of this disclosure advantageously allow for the use of a larger cross-sectional area and quantity of suture or suture tape compared to current assemblies, without requiring external voids in the inserter shaft that increase the risk of insertion failure.

Further examples of the suture anchor insertion assemblies and methods of this disclosure may include one or more of the following, in any suitable combination.

In examples, suture anchor insertion assemblies of this disclosure include a suture anchor having a body with a proximal end and a distal end. The body defines an internal volume. At least one rib extends through the internal volume between the proximal and distal ends of the body. The suture anchor insertion assemblies also include an inserter having a handle assembly and a shaft extending from the handle assembly. An exterior surface of the shaft defines at least one channel extending along a length of the shaft. The distal end of the shaft is configured for insertion within the interior volume of the suture anchor. The suture anchor insertion assemblies also include a flexible member having at least one leg. The at least one leg includes an end region coupled to a needle disposed within a proximal component of the handle assembly. The suture anchor is disposed on the distal end of the shaft such that the at least one rib engages the at least one channel, and the at least one leg of the flexible member extends through the interior volume of the suture anchor and along the at least one channel.

In further examples, the body of the suture anchor has a plurality of turns of threads extending from the proximal end to the distal end of the body, with apertures defined by spaces between the turns of the threads. In examples, the body of the suture anchor further includes a suture bridge at a distal end of the body. The flexible member extends around a distal end of the suture bridge. In examples, the distal end of the shaft includes an open slot defined between proximally-extending prongs and a divider member extending proximally from the open slot. The suture bridge resides within the open slot such that a proximal end of the suture bridge is adjacent to a distal end of the divider member. In examples, the at least one rib, the divider member, and sidewalls of the distal end of the shaft define at least one passage for passage of the at least one leg of the flexible member through the interior volume of the suture anchor. In examples, a cross-section of the divider member has a puzzle-cut. In examples, a central component of the handle assembly is configured to rotate relative to the proximal component of the handle assembly to release the end region of the flexible member and the needle from the handle assembly and/or to release the at least one leg of the flexible member from the at least one channel of the shaft. In examples, an additional flexible member is attached to the at least one leg of the flexible member. In other examples, another leg of the flexible member is attached to the at least one leg of the flexible member.

In examples, methods of inserting a suture anchor into bone of this disclosure include inserting a suture anchor of a suture anchor insertion assembly into bone. The suture anchor insertion assembly includes the suture anchor having a body with a proximal end and a distal end. The body defines an internal volume. At least one rib extends through the internal volume between the proximal and distal ends of the body. The suture anchor insertion assembly also includes an inserter having a handle assembly and a shaft extending from the handle assembly. An exterior surface of the shaft defines at least one channel extending along a length of the shaft. The distal end of the shaft is configured for insertion within the interior volume of the suture anchor. The suture anchor insertion assembly also includes a flexible member having at least one leg. The at least one leg includes an end region coupled to a needle disposed within a proximal component of the handle assembly. The suture anchor is disposed on the distal end of the shaft such that the at least one rib engages the at least one channel, and the at least one leg of the flexible member extends through the interior volume of the suture anchor and along the at least one channel. The central component is rotated relative to the proximal component of the handle assembly, and the inserter is removed from the bone.

In examples, rotating the central component relative to the proximal component allows for release of the end region of the flexible member and the needle from the proximal component of the handle assembly, and/or release of the at least one leg of the flexible member from the at least one channel of the shaft of the handle assembly. In examples, the body of the suture anchor has a plurality of turns of threads extending from the proximal end to the distal end of the body, with apertures defined by spaces between the turns of the threads. In examples, the body of the suture anchor further includes a suture bridge at a distal end of the body. The flexible member extends around a distal end of the suture bridge. In examples, the distal end of the shaft includes an open slot defined between proximally-extending prongs and a divider member extending proximally from the open slot. The suture bridge resides within the open slot such that a proximal end of the suture bridge is adjacent to a distal end of the divider member. In examples, the at least one rib, the divider member, and sidewalls of the distal end of the shaft define at least one passage for passage of the at least one leg of the flexible member through the interior volume of the suture anchor. In examples, a cross-section of the divider member has a puzzle-cut.

In examples, a kit for a surgical repair of this disclosure includes a suture anchor insertion assembly including a suture anchor having a body with a proximal end and a distal end. The body defines an internal volume. At least one rib extends through the internal volume between the proximal and distal ends of the body. The suture anchor insertion assembly also includes an inserter having a handle assembly and a shaft extending from the handle assembly. An exterior surface of the shaft defines at least one channel extending along a length of the shaft. The distal end of the shaft is configured for insertion within the interior volume of the suture anchor. The suture anchor insertion assembly also includes a flexible member having at least one leg. The at least one leg includes an end region coupled to a needle disposed within a proximal component of the handle assembly. The suture anchor is disposed on the distal end of the shaft such that the at least one rib engages the at least one channel, and the at least one leg of the flexible member extends through the interior volume of the suture anchor and along the at least one channel. The kit also includes another suture anchor insertion assembly different from the suture anchor insertion assembly, and a drill. In examples, the kit also includes a guide.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein.

DETAILED DESCRIPTION

Figure 1:
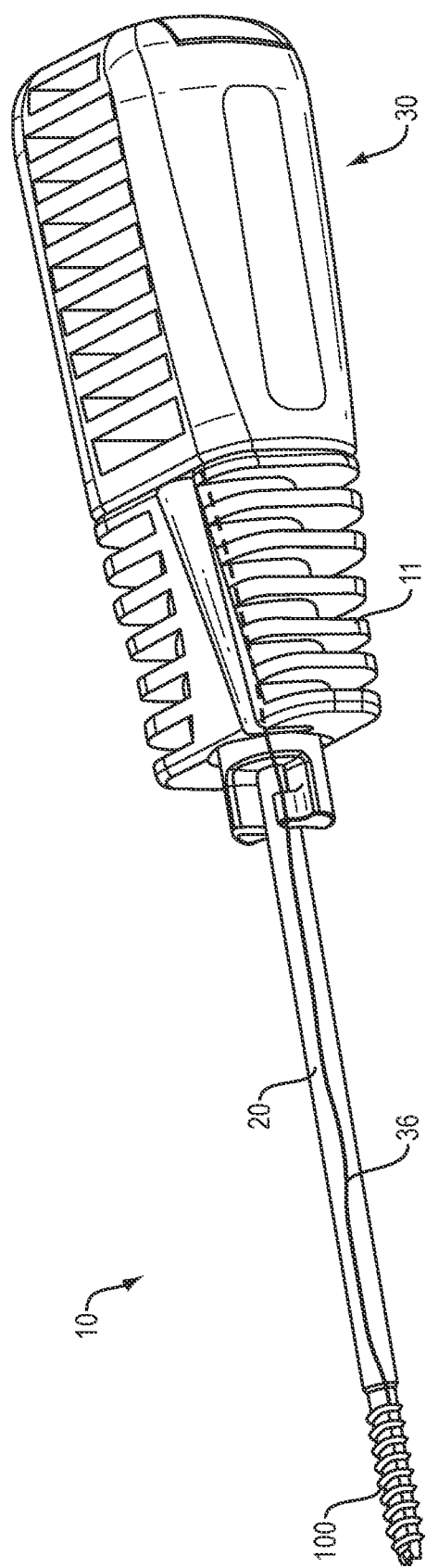
FIG. 1 illustrates an example of a suture anchor insertion assembly of this disclosure in an assembled view.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts.

FIG. 1 shows an example of a suture anchor insertion assembly 10 of this disclosure in an assembled view. A surgeon can use the suture anchor insertion assembly 10 for inserting a suture anchor 100 into bone, for example, during an Achilles tendon repair. As shown in FIG. 1, the suture anchor insertion assembly 10 generally includes an inserter 30 having a shaft 20 for engaging the suture anchor 100. In examples, the suture anchor 100 has an open architecture, as further described below. A flexible member, such as suture tape or a suture 36, extends from the suture anchor 100 along an outer surface of the shaft 20 to the handle 11 of the inserter 30. Unlike some prior art inserter shafts, the shaft 20 does not include a central passage extending through a center of the shaft 20 for passage of the suture 36.

Figure 2A:
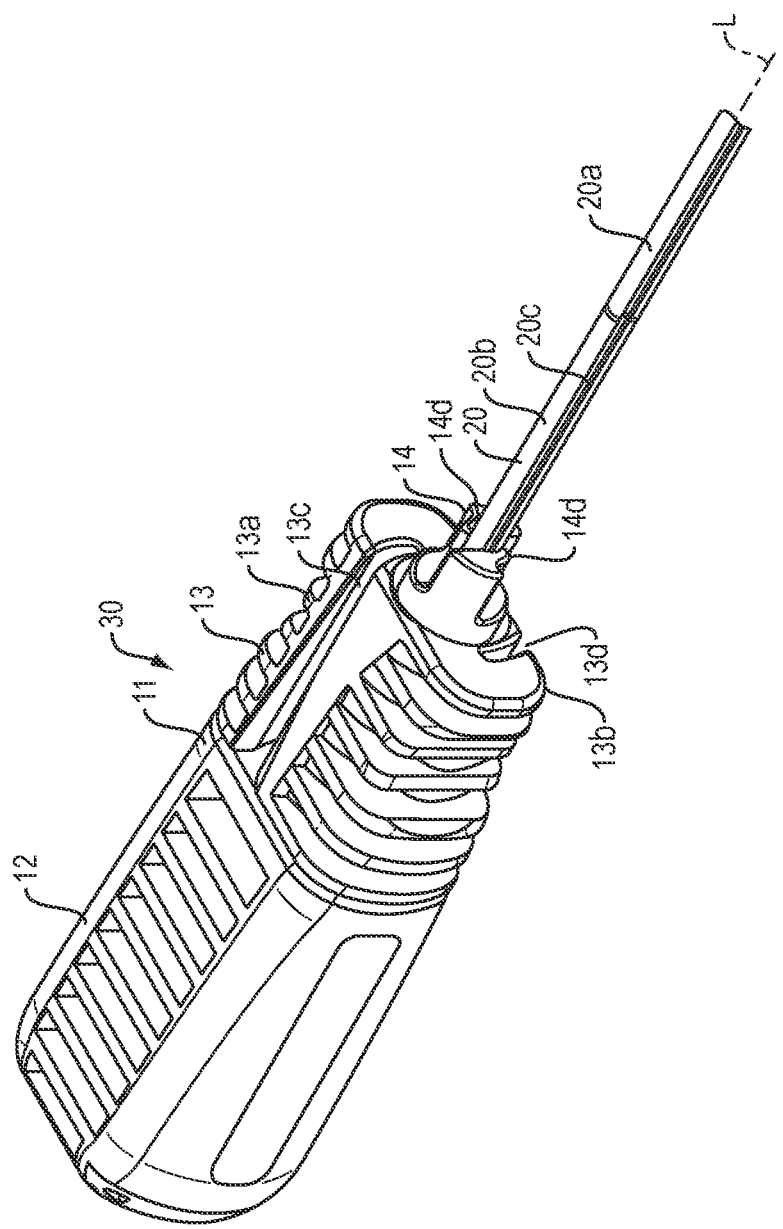
FIGS. 2A-C illustrate examples of the inserter of the suture anchor insertion assembly of FIG. 1.

FIG. 2A shows an example of the inserter 30 of the present disclosure in a perspective view. As shown in FIG. 2A, the shaft 20 of the inserter 30 includes a distal end 20a configured to engage the suture anchor, a proximal end 20b coupled to the handle 11, and at least one external channel 20c extending along a length of the shaft 20. In examples, the at least one channel 20c comprises two opposing channels 20c, or more or fewer than two channels 20c. The handle 11 generally includes a proximal component 12, a central component 13, and a distal component 14. The proximal component 12 houses needles pre-attached to suture, as further described below. The central component 13 rotates relative to the proximal component 12 along the longitudinal axis L of the handle 11. The central component 13 includes a top surface 13a having a groove 13c, and a bottom surface 13b having a groove 13d. The grooves 13c, 13d allow passage of the suture across the respective surfaces 13a, 13b of the central component 13 to the proximal component 12. The distal component 14 includes suture retainers 14d that extend within the channels 20c to retain the suture within the channels 20c prior to advancing the suture anchor into bone.

Figure 2B:
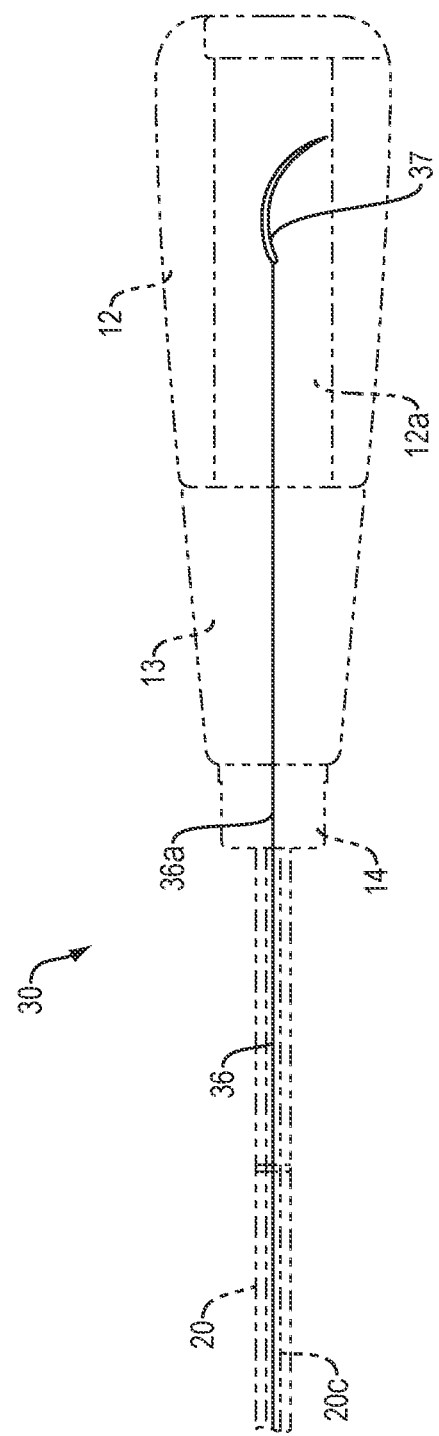

FIG. 2B illustrates the inserter 30 in a transparent view, showing needles 37 coupled to the ends 36a of the suture 36. The ends 36a of the suture 36 house within the channels 20c of the shaft 20 and extend through the grooves 13c, 13d (FIG. 2A) of the central component 13 and into holes 12a in the proximal component 12. The central component 13, the proximal component 12, and the ends 36a of the suture 36 interact to allow for retaining the ends 36a of the suture 36 in the grooves 13c, 13d, as further described below. Furthermore, the holes 12a of the proximal component 12 retain the needles 37 due to the central component 13 covering the holes 12a before rotation of the central component 13 relative to the proximal component 12.

Figure 2C:
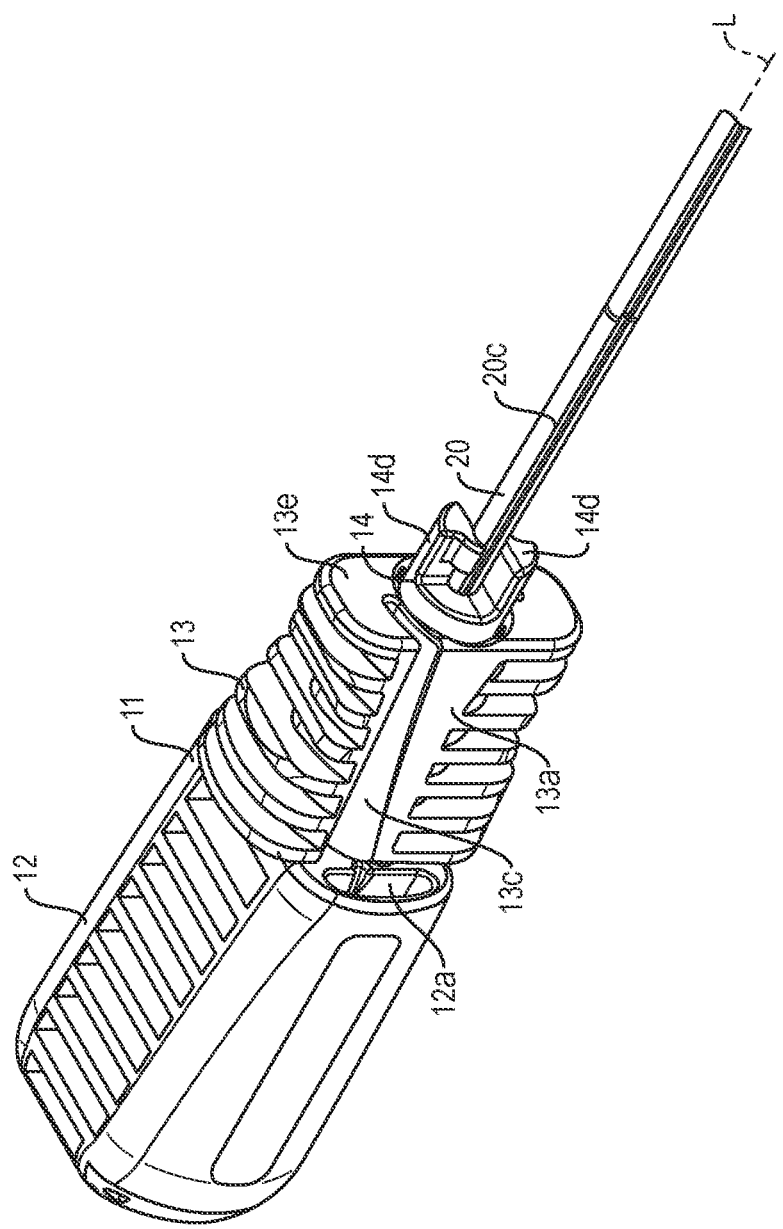

FIG. 2C shows the central component 13 rotated at about a 90° angle relative to the proximal component 12, with other angles between about 0° and about 90° also within the scope of this disclosure. Rotating the central component 13 allows for removing the suture retainers 14d from the channels 20c of the shaft 20 and uncovering of the holes 12a in the proximal component 12. This rotation allows for removing the suture and needles from the channels 20c, the grooves 13c, 13d and the holes 12a. U.S. Pat. No. 9,050,077 to Smith & Nephew, Inc. (Memphis, TN), incorporated herein by reference, shows and describes other non-limiting examples of handles 11 configured for housing needles pre-attached to suture.

Figure 3A:
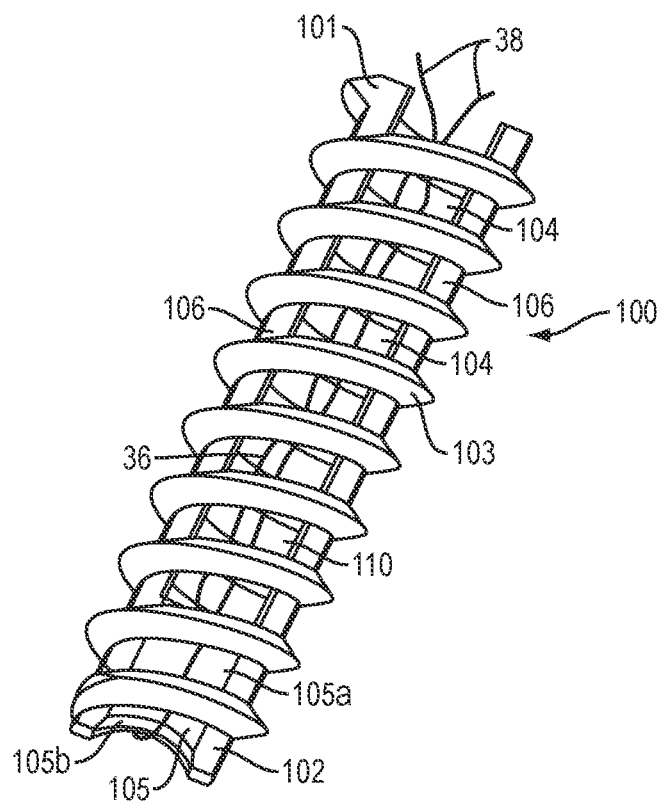
FIG. 3A illustrates an example of the suture anchor of the suture anchor insertion assembly of FIG. 1.

FIG. 3A shows an example of the suture anchor 100 of this disclosure in a detailed view. The suture anchor 100 includes a proximal end 101 and a distal end 102. A majority of the suture anchor 100 includes screw threads 103 in the form of an open helical coil. The open helical coil has a connected series of continuous, regularly spaced turns of the threads 103 extending in a helical or spiral form substantially from the proximal end 101 to the distal end 102 of the suture anchor 100 with apertures 104 defined by spaces between the turns of the threads 103. The suture anchor 100 defines an internal volume 110 communicating with the region exterior to the suture anchor 100 through the apertures 104. Additionally, longitudinally-extending ribs 106 extend along the interior volume 110 of the suture anchor 100. For the purposes of this disclosure, two longitudinally-extending ribs 106 extend along the interior volume 110. However, the disclosure may include more or fewer than two ribs 106. The distal end 102 of the suture anchor 100 also includes a suture bridge 105 that extends between the ribs 106 along a partial length of the suture anchor 100. The suture bridge 105 includes a proximal end 105a and a distal end 105b. In examples, the ribs 106 extend evenly with or distally past the suture bridge 105. However, in other examples, the distal end 105b of the suture bridge may extend distally past the ribs 106. In examples, the distal end 105b of the suture bridge 105 has a concave shape. However, the disclosure includes other shapes of the distal end 105b of the suture bridge 105, such as bulbous or flat. The suture anchor 100 houses the suture 36 such that the suture 36 extends around the distal end 105b of the suture bridge 105 and legs 38 of suture 36 extend through the interior volume 110 of the suture anchor 100. U.S. Pat. No. 9,949,820 to Smith & Nephew, Inc. (Memphis, TN), incorporated herein by reference, shows and describes other non-limiting examples of suture anchors configured for use with the suture anchor insertion assemblies 10 of this disclosure.

Figure 3B:
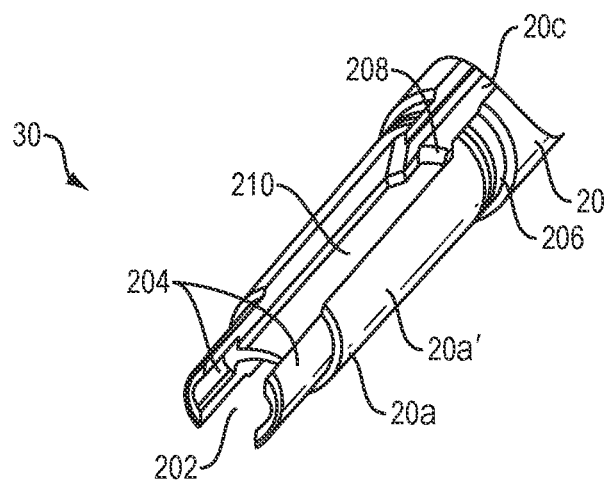
FIG. 3B illustrates an example of the distal end of the inserter for use with the suture anchor of FIG. 3A.

Turning now to FIG. 3B, the distal end 20a of the shaft 20 of the inserter 30 includes an open slot 202 defined by distally-extending, semi-circular prongs 204. The disclosure contemplates two distally-extending prongs 204, as well as more or fewer than two prongs 204. The channels 20c extend proximally from the slot 202 on each side of a divider member 210 extending along the distal end 20a of the shaft 20. The distal end 20a of the shaft 20 has a stepped-down diameter such that the distal end 20a of the shaft 20 has a smaller diameter than the diameter of the remainder of the shaft 20. Thus, an annular neck portion 206 forms between the distal end 20a of the shaft 20 and the remainder of the shaft 20. A circle defined by the prongs 204, moreover, has smaller diameter than the diameter of the distal end 20a of the shaft 20 and the remainder of the shaft 20. The portion of the channel 20c in the distal end 20a of the shaft 20 has a greater depth than the portion of the channel 20c in the remainder of the shaft 20 in order to house the ribs 106 of the suture anchor 100. Thus, a first wall 208 forms between the portion of the channel 20c extending through the distal end 20a of the shaft 20 and the portion of the channel 20c extending through the remainder of the shaft 20. Sidewalls 20a' of the distal end 20a of the shaft and the divider member 210 extending from the first wall 208 define the portion of the channel 20c extending through the distal end 20a of the shaft. In examples, the divider member 210 integrally forms with the sidewalls 20a'.

Figure 3C:
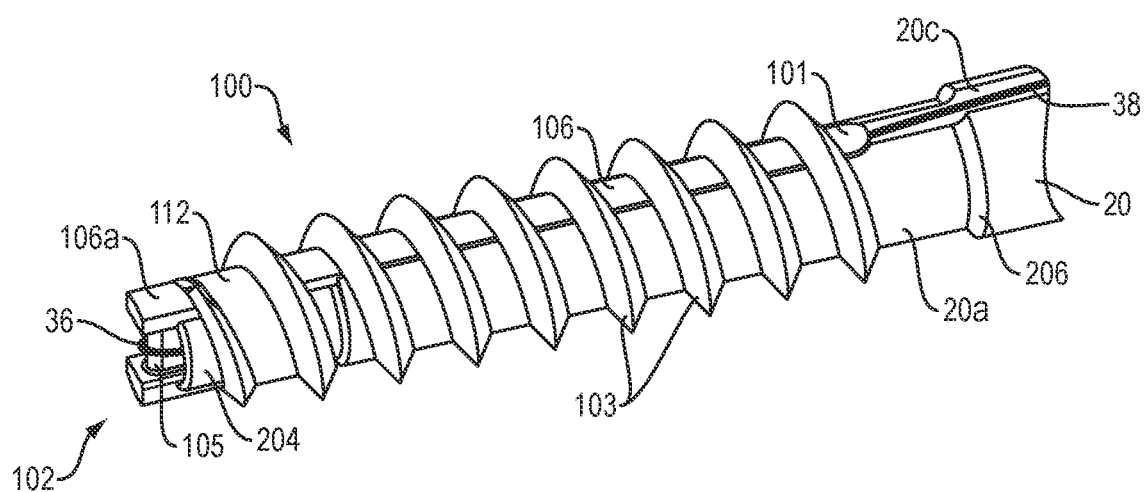
FIG. 3C illustrates an assembly of the suture anchor of FIG. 3A and the inserter of FIG. 3B.

As shown in FIG. 3C, the suture anchor 100 sits on the distal end 20a of the shaft 20 such that the suture bridge 105 houses within the slot 202, the ribs 106 house within the channels 20c, and the proximal end 105b of the suture bridge 105 nears the distal end of the divider member 210. Webbing 112 may extend between turns of the thread 103 at a region of the suture anchor 100 engaged with the prongs 204 to increase the rigidity of the distal end 102 of the suture anchor 100 and improve insertion performance of the suture anchor 100. The suture 36 extends around the distal end 105a of suture bridge 105 and through the interior volume 110 of the suture anchor 100 such that the legs 38 of the suture 36 emerge from the proximal end 101 of the suture anchor 100 within the channels 20c in a region between the proximal end 101 of the suture anchor 100 and the neck portion 206 of the shaft 20. The suture anchor 100 also sits on the distal end 20a of the shaft 20 such that no gaps or voids form between the threads 103 of the suture anchor 100 and the distal end 20a of the shaft 20.

Figure 3D:
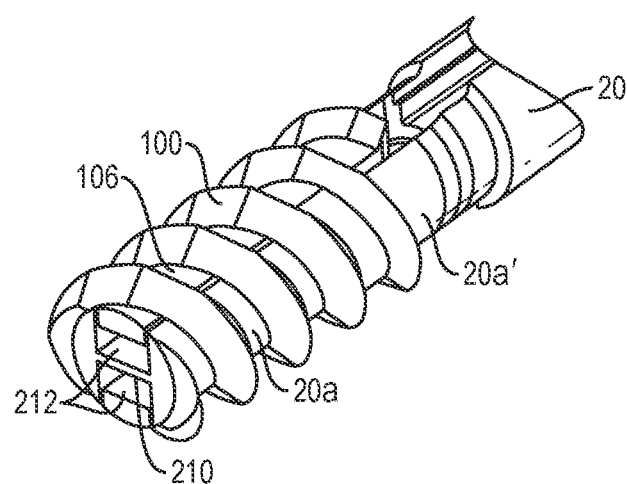
FIG. 3D illustrates a cross-section of the assembly of FIG. 3C.

FIG. 3D shows a cross-section of the suture anchor 100 disposed on the distal end 20a of the shaft 20. As shown, the ribs 106 of the suture anchor 100, the sidewalls 20a' of the distal end 20a of the shaft 20, and opposing surfaces of the divider member 210 define passages 212. In the example of FIG. 3D, the divider member 210 extends between the sidewalls 20a' of the distal end 20a of the shaft 20 such that each passage 212 has a substantially equal area. The passages 212 allow for the passage of a respective leg 38 of the suture 36 (not shown) extending around the suture bridge 105.

Figure 4B:
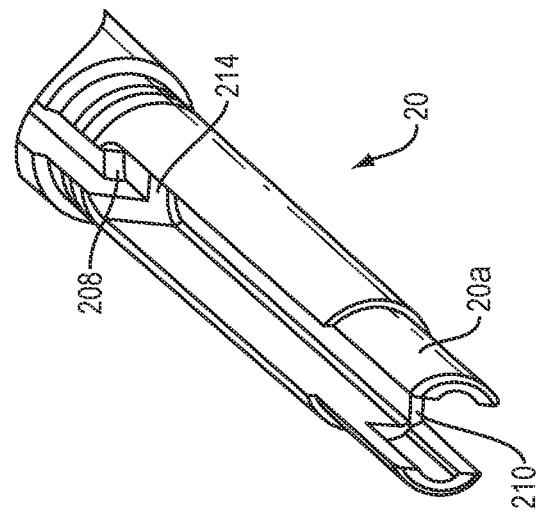
FIGS. 4A and 4B illustrate another example of a suture anchor/inserter assembly (FIG. 4A) and the distal end of the inserter thereof (FIG. 4B)
Figure 4A:
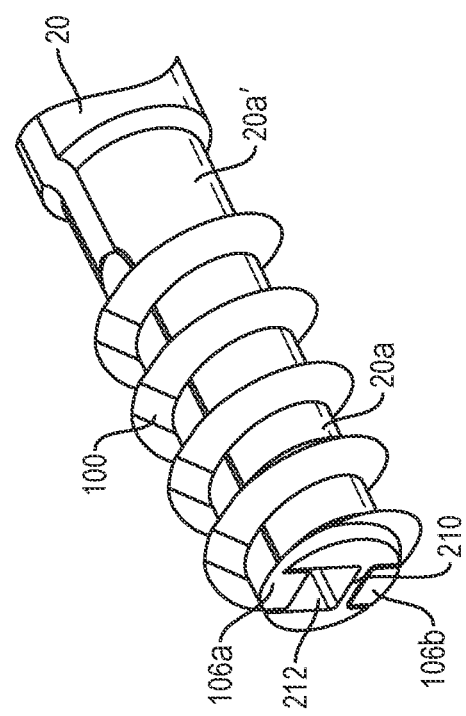

FIG. 4A shows another example of a cross-section of the suture anchor 100 disposed on the distal end 20a of the shaft 20 of this disclosure. In the example of FIG. 4A, one of the ribs 106a of the suture anchor 100, the sidewalls 20a', and a surface of the divider member 210 define only a single passage 212. In this example, the divider member 210 advantageously provides support for the other of the ribs 106b to improve insertion performance of the suture anchor 100. The passage 212 allows for the passage of both respective legs 38 of the suture 36 extending around the suture bridge 105. Compared with the example of FIG. 3D, the single passage 212 advantageously allows for a greater amount of suture or suture tape to pass through the passage 212. Additionally, the example of FIG. 4A allows for aligning the suture or suture tape with the suture bridge 105 to facilitate suture slide within the passage 212.

FIG. 4B shows the configuration of the distal end 20a of the shaft 20 of FIG. 4A before coupling to the suture anchor 100. In particular, FIG. 4B shows a second wall 214 distal to the first wall 208 formed by the offset placement of the divider member 210 relative to a center of the shaft 20. The divider member 210 extends distally from the second wall 214 to approach the proximal end 105a of the suture bridge 105.

Figure 5B:
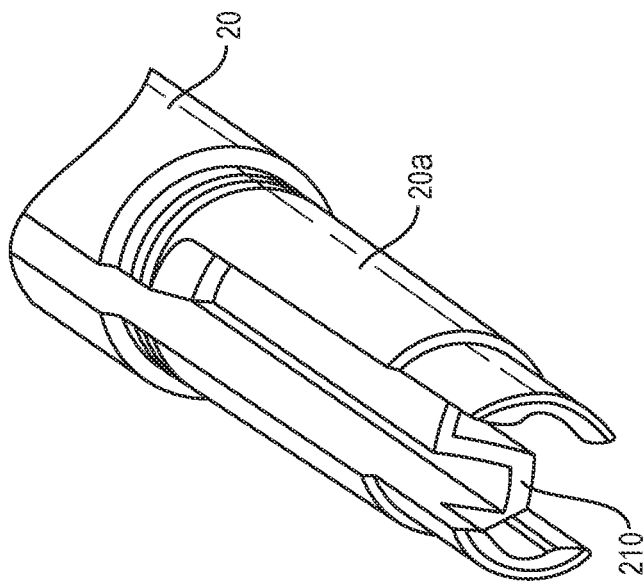
FIGS. 5A and 5B illustrate another example of a suture anchor/inserter assembly (FIG. 5A) and the distal end of the inserter thereof (FIG. 5B)
Figure 5A:
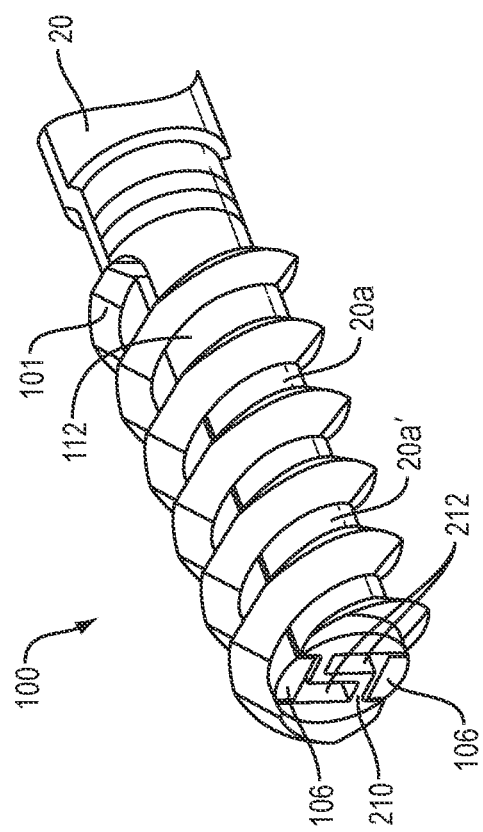

FIG. 5A shows another example cross-section of the suture anchor 100 disposed on the distal end 20a of the shaft 20 of this disclosure. In the example of FIG. 5A, a cross-section of the divider member 210 has a "puzzle cut" and extends between the sidewalls 20a' such that each passage 212 has a substantially equal area. In this example, the divider member 210 advantageously provides partial support for both of the ribs 106 to improve the insertion performance of the suture anchor 100. The passages 212 allow for the passage of respective legs 38 of the suture 36 extending around the suture bridge 105. Webbing 112 may extend between turns of the thread 103 at a region of the anchor 100 engaged with the distal end 20a of the shaft 20 to increase the rigidity of the proximal end 101 of the suture anchor 100 and improve insertion performance of the suture anchor 100. Compared with the example of FIG. 3A, the example of FIG. 5A allows for aligning the suture or suture tape with the suture bridge 105 to facilitate suture slide within the passages 212. FIG. 5B shows the configuration of the distal end 20a of the shaft 20 of FIG. 5A before coupling to the suture anchor 100.

Figure 6A:
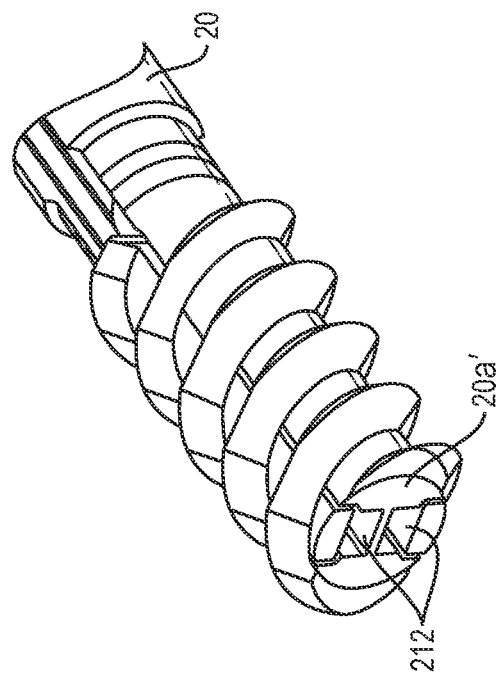
FIGS. 6A and 6B illustrate additional examples of a suture anchor/inserter assembly.
Figure 6B:
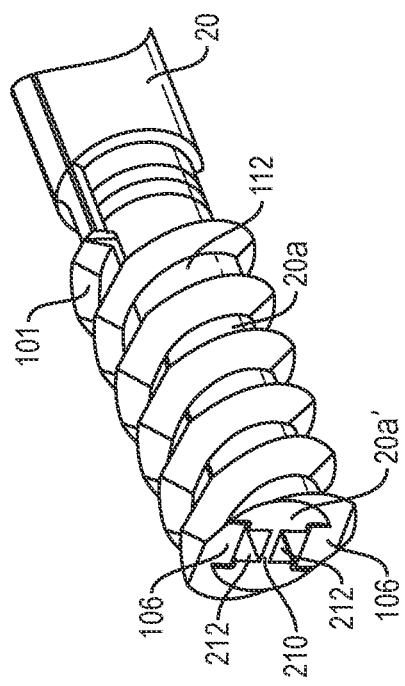

FIG. 6A shows another example cross-section of the suture anchor 100 disposed on the distal end 20a of the shaft 20 of this disclosure. In the example of FIG. 6A, a cross-section of the sidewalls 20a' have a "dovetail" cut. The divider member 210 extends between the sidewalls 20a' such that each passage 212 has a substantially equal area. In this example, the sidewalls 20a' provide partial support for both of the ribs 106 to advantageously improve insertion performance of the suture anchor 100. The passages 212 allow for the passage of respective legs 38 of the suture 36 extending around the suture bridge 105. Webbing 112 may extend between turns of the thread 103 at a region of the anchor 100 engaged with the distal end 20a of the shaft 20 to increase the rigidity of the proximal end 101 of the suture anchor 100 and improve insertion performance of the suture anchor 100. The dovetail cut of the sidewalls 20a' may have any shape, angle or configuration, for example, as shown in FIG. 6B.

Figure 7A:
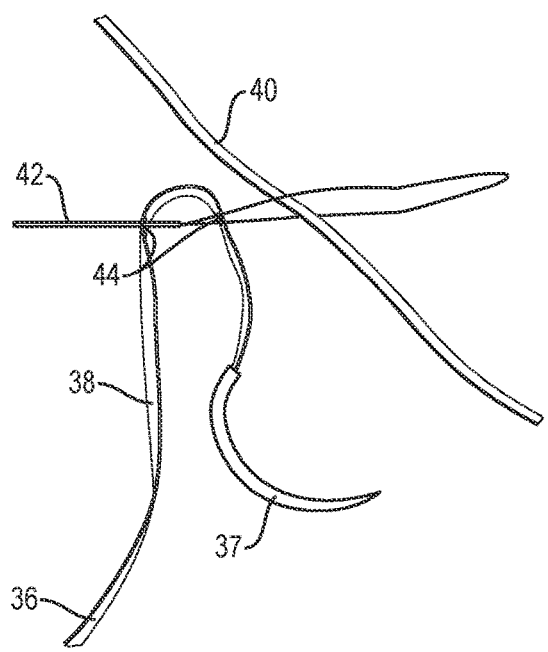
FIGS. 7A-C illustrate a method of attaching additional sutures to the suture anchor insertion assembly of FIG. 1.
Figure 7B:
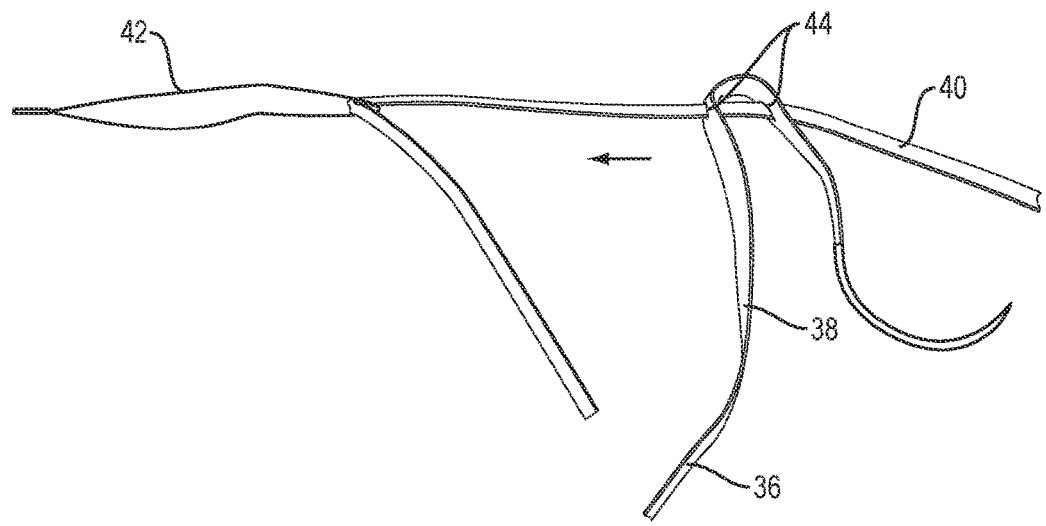
Figure 7C:
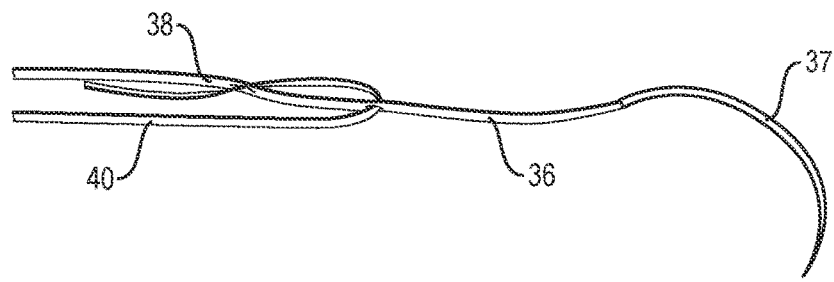

Turning now to FIG. 7A, in examples, the suture anchor insertion assembly 10 of this disclosure may include an additional suture tape or suture 40 preassembled to the legs 38 of the suture 36. Preassembly of the additional suture 40 to the legs 38 of the suture 36 allows the surgeon to use the additional suture 40 in the repair with a single suture anchor while requiring fewer passes of the needle 37 through the tissue. As shown in FIG. 7A, the preassembly includes initially passing a loop of a suture passer 42 through one or more regions 44 of the leg 38 of the suture 36. The additional suture 40 is then passed through the loop of the suture passer 42. As shown in FIG. 7B, the suture passer 42 is then used to pull the additional suture 40 through the regions 44 of the leg 38 of the suture 36. Thus, as shown in FIG. 7C, one pass of the needle 37 through tissue can carry one or more additional sutures 40 in addition to the limb 38 of the suture 36.

Figure 8A:
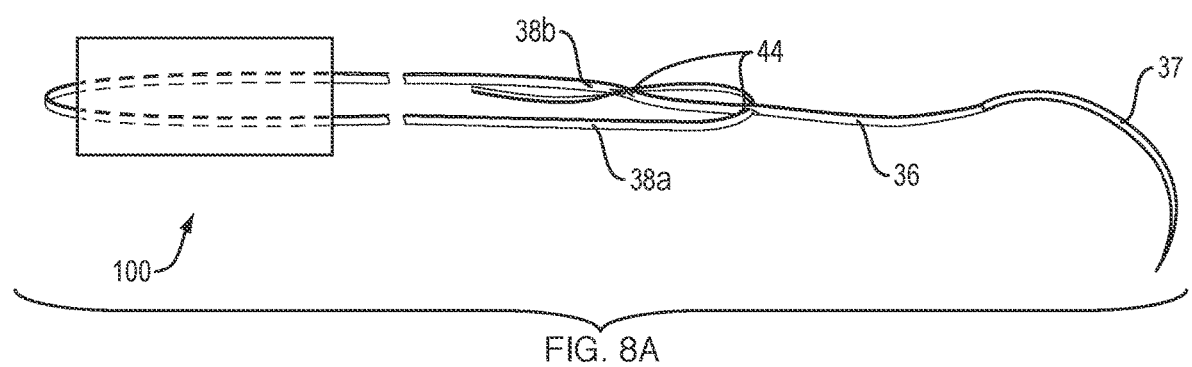
FIGS. 8A-D illustrate a method of attaching one suture limb to another suture limb of the suture anchor insertion assembly of FIG. 1.
Figure 8B:
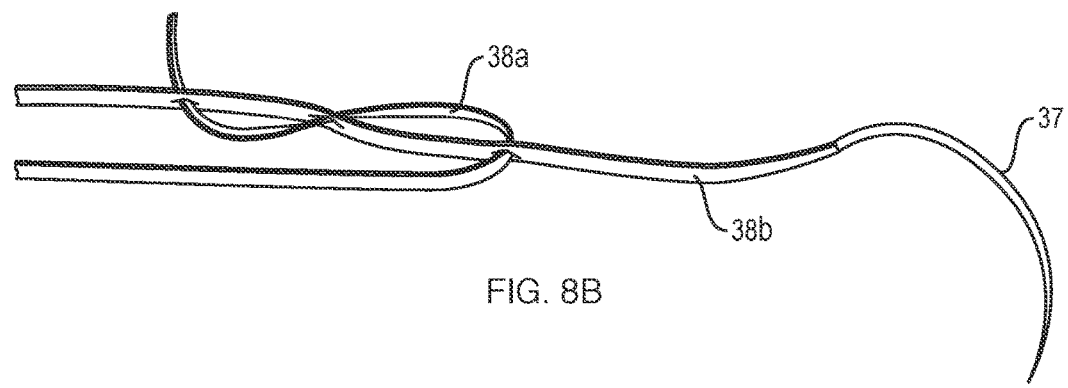
Figure 8C:
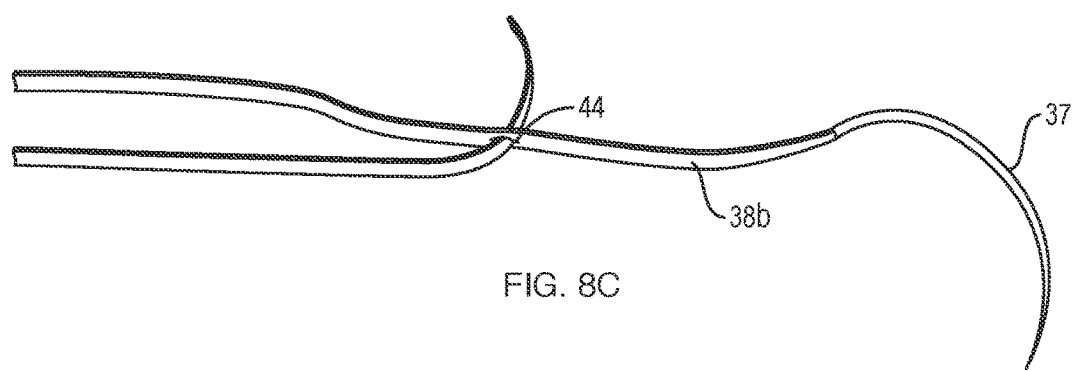
Figure 8D:
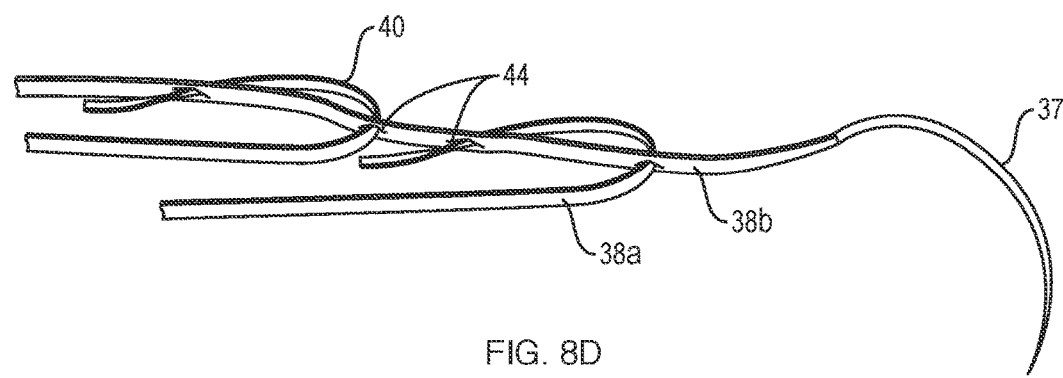

In alternative examples, shown in FIGS. 8A-C, rather than attaching an additional suture to the legs of the suture 36, the preassembly may instead include attaching a first leg 38a of the suture 36 extending from the suture anchor 100 to a second leg 38b of the suture 36 extending around the suture bridge of the suture anchor 100. In examples, the first leg 38a can pass through two regions 44 of the second leg 38b (FIG. 8A). In other examples, the first leg 38a can pass through three or more regions 44 of the second leg 38b (FIG. 8B). In further examples, the first leg 38a can pass through only one region 44 of the second leg 38b (FIG. 8C). In other examples, shown in FIG. 8D, both of an additional suture 40 and the first leg 38a can pass through regions 44 of the second leg 38b.

Figure 9:
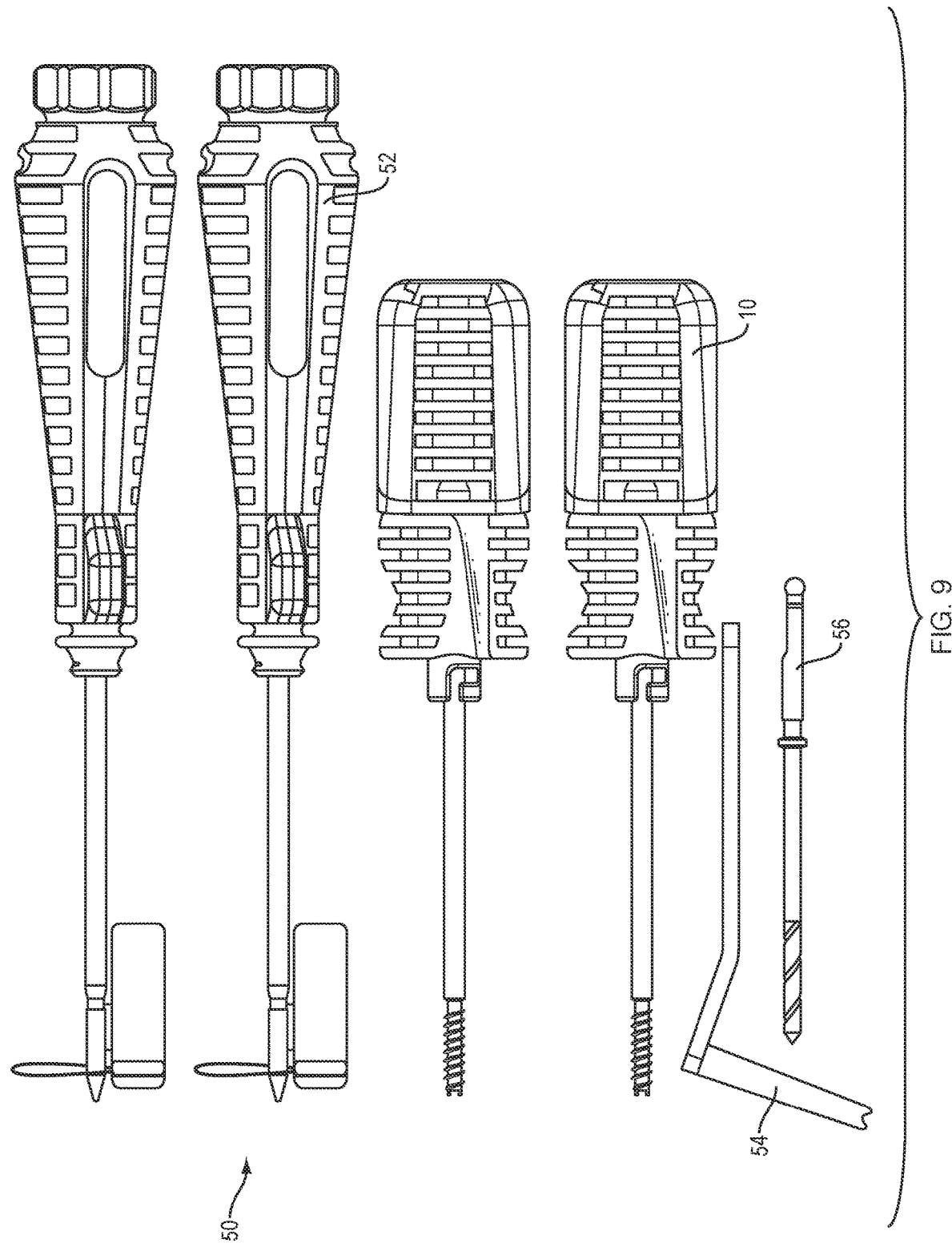
FIG. 9 is an example of a kit including the suture anchor insertion assembly of FIG. 1.

As shown in FIG. 9, a kit 50 for a surgical repair, such as an Achilles tendon repair, may include at least one suture anchor insertion assembly 10 of this disclosure. In examples, the kit 50 may also include a suture anchor insertion assembly 52 different from the suture anchor insertion assembly 10 of this disclosure. In examples, the kit 50 may also include at least a guide 54 and/or a drill 56 for use in the surgical repair.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

The invention claimed is:

1. A suture anchor insertion assembly comprising:
a suture anchor comprising:
a body having a proximal end and a distal end, the body defining an internal volume; and
at least one rib extending through the internal volume between the proximal and distal ends of the body;
an inserter comprising:
a handle assembly; and
a shaft extending from the handle assembly, an exterior surface of the shaft defining at least one channel extending along a length of the shaft, a distal end of the shaft configured for insertion within the internal volume of the suture anchor, the distal end of the shaft comprising an open slot defined between proximally extending prongs and a divider member extending proximally from the open slot;
at least one wall formed between the divider member and the at least one channel, the at least one wall positioned between the prongs at a proximal end of the prongs; and
a flexible member comprising at least one leg, the at least one leg having an end region coupled to a needle disposed within a proximal component of the handle assembly;

wherein the suture anchor is disposed on the distal end of the shaft such that the at least one rib engages the at least one channel, and the at least one leg of the flexible member extends through the internal volume of the suture anchor and along the at least one channel; and wherein the at least one leg of the flexible member extends along an outer surface of the divider member and over the at least one wall to the at least one channel.

2. The suture anchor insertion assembly of claim 1, wherein the body of the suture anchor further comprises a plurality of turns of threads extending from the proximal end to the distal end of the body, with apertures defined by spaces between the turns of the threads.

3. The suture anchor insertion assembly of claim 1, wherein the body of the suture anchor further comprises a suture bridge at the distal end of the body, and wherein the flexible member extends around a distal end of the suture bridge.

4. The suture anchor insertion assembly of claim 3, wherein the suture bridge resides within the open slot of the shaft such that a proximal end of the suture bridge is adjacent to a distal end of the divider member.

5. The suture anchor insertion assembly of claim 1, wherein the at least one rib, the divider member, and sidewalls of the distal end of the shaft define at least one passage for passage of the at least one leg of the flexible member through the interior internal volume of the suture anchor.

6. The suture anchor insertion assembly of claim 1, wherein a cross-section of the divider member has a puzzle-cut.

7. The suture anchor insertion assembly of claim 1, wherein a central component of the handle assembly is configured to rotate relative to the proximal component of the handle assembly to release the end region of the flexible member and the needle from the handle assembly.

8. The suture anchor insertion assembly of claim 1, wherein a central component of the handle assembly is configured to rotate relative to the proximal component of the handle assembly to release the at least one leg of the flexible member from the at least one channel of the shaft.

9. The suture anchor insertion assembly of claim 1, wherein an additional flexible member is attached to the at least one leg of the flexible member.

10. The suture anchor insertion assembly of claim 1, wherein another leg of the flexible member is attached to the at least one leg of the flexible member.

11. A method of inserting a suture anchor into bone comprising:
inserting a suture anchor of a suture anchor insertion assembly into bone, the suture anchor insertion assembly comprising:
the suture anchor comprising a body having a proximal end and a distal end, the body defining an internal volume; and at least one rib extending through the internal volume between the proximal and distal ends of the body;
an inserter comprising a handle assembly and a shaft extending from the handle assembly, an exterior surface of the shaft defining at least one channel extending along a length of the shaft, a distal end of the shaft configured for insertion within the internal volume of the suture anchor, the distal end of the shaft comprising an open slot defined between proximally extending prongs and a divider member extending proximally from the open slot;
at least one wall formed between the divider member and the at least one channel, the at least one wall positioned between the prongs at a proximal end of the prongs; and
a flexible member comprising at least one leg, the at least one leg having an end region coupled to a needle disposed within a proximal component of the handle assembly;
wherein the suture anchor is disposed on the distal end of the shaft such that the at least one rib engages the at least one channel, and the at least one leg of the flexible member extends through the internal volume of the suture anchor and along the at least one channel; and
wherein the at least one leg of the flexible member extends along an outer surface of the divider member and over the wall to the at least one channel;
rotating a central component relative to the proximal component of the handle assembly; and
removing the inserter from the bone.

12. The method of claim 11, wherein rotating the central component relative to the proximal component allows for release of the end region of the flexible member and the needle from the proximal component of the handle assembly.

13. The method of claim 11, wherein rotating the central component relative to the proximal component allows for release of the at least one leg of the flexible member from the at least one channel of the shaft of the handle assembly.

14. The method of claim 11, wherein the body of the suture anchor further comprises a plurality of turns of threads extending from the proximal end to the distal end of the body, with apertures defined by spaces between the turns of the threads.

15. The method of claim 11, wherein the body of the suture anchor further comprises a suture bridge at the distal end of the body, and wherein the flexible member extends around a distal end of the suture bridge.

16. The method of claim 15, wherein the suture bridge resides within the open slot of the shaft such that a proximal end of the suture bridge is adjacent to a distal end of the divider member.

17. The method of claim 11, wherein the at least one rib, the divider member, and sidewalls of the distal end of the shaft define at least one passage for passage of the at least one leg of the flexible member through the internal volume of the suture anchor.

18. The method of claim 11, wherein a cross-section of the divider member has a puzzle-cut.

19. A kit for a surgical repair comprising:
a suture anchor insertion assembly comprising:
a suture anchor comprising:
a body having a proximal end and a distal end, the body defining an internal volume; and
at least one rib extending through the internal volume between the proximal and distal ends of the body;
an inserter comprising:
a handle assembly; and
a shaft extending from the handle assembly, an exterior surface of the shaft defining at least one channel extending along a length of the shaft, a distal end of the shaft configured for insertion within the internal volume of the suture anchor, the distal end of the shaft comprising an open slot defined between proximally extending prongs and a divider member extending proximally from the open slot:

at least one wall formed between the divider member and the at least one channel, the at least one wall positioned between the prongs at a proximal end of the prongs; and a flexible member comprising at least one leg, the at least one leg having an end region coupled to a needle disposed within a proximal component of the handle assembly;

wherein the suture anchor is disposed on the distal end of the shaft such that the at least one rib engages the at least one channel, and the at least one leg of the flexible member extends through the internal volume of the suture anchor and along the at least one channel; and wherein the at least one leg of the flexible member extends along an outer surface of the divider member and over the wall to the at least one channel;

another suture anchor insertion assembly different from the suture anchor insertion assembly; and a drill.

20. The kit of claim 19, wherein the kit further includes a guide.

* * * * *